US010309955B2

(12) United States Patent
Chang et al.

(10) Patent No.: US 10,309,955 B2
(45) Date of Patent: Jun. 4, 2019

(54) ROTATING DEVICE FOR BIOLOGICAL DETECTION

(71) Applicant: QUANTA STORAGE INC., Taoyuan (TW)

(72) Inventors: Chen-Fu Chang, Taoyuan (TW); Chien-Hui Hsu, Taoyuan (TW); Sheng-Wen Chiu, Taoyuan (TW); Chuan-Tsung Feng, Taoyuan (TW)

(73) Assignee: QUANTA STORAGE INC., Taoyuan (TW)

( * ) Notice: Subject to any disclaimer, the term of this patent is extended or adjusted under 35 U.S.C. 154(b) by 414 days.

(21) Appl. No.: 15/233,960

(22) Filed: Aug. 11, 2016

(65) Prior Publication Data

US 2017/0059545 A1    Mar. 2, 2017

(30) Foreign Application Priority Data

Aug. 26, 2015    (CN) .......................... 2015 1 0529123

(51) Int. Cl.
*B01L 3/00*    (2006.01)
*C12M 3/00*    (2006.01)
*G01N 33/487*    (2006.01)
*G01N 35/00*    (2006.01)
*G01N 21/59*    (2006.01)

(52) U.S. Cl.
CPC .......... *G01N 33/487* (2013.01); *B01L 3/5027* (2013.01); *G01N 21/59* (2013.01); *G01N 35/00069* (2013.01); *G01N 2035/00495* (2013.01)

(58) Field of Classification Search
CPC ......... C12M 23/48; C12M 23/46; B01L 9/52; B01L 9/523; B01L 9/527
See application file for complete search history.

(56) References Cited

U.S. PATENT DOCUMENTS

| 6,323,035 | B1* | 11/2001 | Kedar | ................ | G01N 35/0099 414/277 |
| 2006/0105450 | A1* | 5/2006 | Owen | ................ | G01N 35/0099 435/303.3 |
| 2006/0128005 | A1* | 6/2006 | Hasegawa | ............... | C12M 23/10 435/286.2 |
| 2006/0246487 | A1* | 11/2006 | Oh | .................... | B01L 3/502715 435/6.12 |
| 2008/0141288 | A1* | 6/2008 | Ishikawa | ............ | G11B 17/0404 720/601 |

(Continued)

*Primary Examiner* — Nathan A Bowers
(74) *Attorney, Agent, or Firm* — Winston Hsu

(57) ABSTRACT

A rotating device includes a rotating shaft, a rotating disc, a left clamping disc, a right clamping disc, an upper clamping disc, and a recovering component. The upper clamping disc, the left clamping disc, and the right clamping disc are sleeved on the rotating shaft. The upper clamping disc fixes the rotating disc, the left clamping disc, and the right clamping disc on the rotating shaft. The recovering component abuts between a side of the left clamping disc and a side of the right clamping disc. A clamping zone is formed between the other side of the left clamping disc and the other side of the right clamping disc for clamping the detecting disc, and an overlapping zone is formed between the side of the left clamping disc and the side of the right clamping disc and opposite to the clamping zone.

10 Claims, 6 Drawing Sheets

(56) References Cited

U.S. PATENT DOCUMENTS

| | | | | |
|---|---|---|---|---|
| 2008/0145924 | A1* | 6/2008 | Kobayashi | B01L 3/50855 435/294.1 |
| 2009/0125922 | A1* | 5/2009 | Yokoe | G11B 17/051 720/601 |
| 2010/0287575 | A1* | 11/2010 | Susumago | G11B 17/051 720/621 |
| 2010/0290868 | A1* | 11/2010 | Virag | G02B 21/34 414/222.01 |

* cited by examiner

US 10,309,955 B2

ROTATING DEVICE FOR BIOLOGICAL DETECTION

BACKGROUND OF THE INVENTION

1. Field of the Invention

The present invention relates to a biological detection system, and more particularly, to a rotating device for biological detection and capable of rotating a detecting disc carrying an object under test.

2. Description of the Prior Art

With development of medical science and technology, there are more and more methods for biological detection. A detecting disc is adapted for biological particles of an object under test to be optically detected easily. Furthermore, different objects under test can be optically detected on the same detecting disc at the same time, which can analyze the objects under test automatically and rapidly. Therefore, it has become one of mainstream technologies of the biological detection.

A conventional biological detection system usually utilizes a circular detecting disc whereon a plurality of testing channels is formed for receiving objects under test, such as blood, and labeling reagents including fluorescent particles or magnetic particles. The detecting disc is fixed on a rotating device. When it is desired to detect the objects, i.e., the blood, the rotating device rotates the detecting disc rapidly. Since cellular pellets and plasma of the blood have different weights, the cellular pellets and the plasma can be separated by a generated centrifugal force. The plasma separated from the cellar pellets flows into detecting grooves of the testing channels to be mixed with the labeling reagents thoroughly, so that pathogen particles of the plasma can be labeled by the fluorescent particles or magnetic particles. Therefore, a detecting result can be determined according to the number of the labeled pathogen particles in the detecting grooves.

More specifically, the conventional biological detection system includes an optical pickup head disposed on a position corresponding to the detecting grooves. When the rotating device rotates the detecting disc for a predetermined period, the plasma is separated from the cellular pellets and mixed with the labeling reagents thoroughly. The optical pickup head is controlled to emit light to the detecting grooves of the testing channels. Since luminous flux of the light passing through the detecting grooves is related to the number of the labeled pathogen particles in the detecting grooves, the biological detection system can determine the detecting result according to signal strength generated from the luminous flux of the light received by the optical pickup head or a scattered light receiver.

However, since the conventional detecting disc has a plurality of testing channels, when the object under test is received in one of the testing channels, the other testing channels will be contaminated during detection. Therefore, the detecting disc cannot be reused again and should be discarded, which wastes resources.

Please refer to FIG. 6. FIG. 6 is a schematic diagram of another conventional biological detection system. As shown in FIG. 6, a plurality of sliding slot 2 is formed on a frame 1. Each of the plurality of sliding slot 2 can receive one detecting disc 3, and one testing channel 4 is formed on each of the detecting disc 3. When it is desired to detect the detecting disc 3, the detecting disc 3 is selectively to be accommodated in one of the slots 2. Afterward, the frame 1 starts to rotate for the biological detection. During the biological detection, the other detecting discs 3 will not be contaminated, which achieves a purpose of detecting a small number of the objects under test.

However, even although it can detect the object under test accommodated in only one single testing channel, the weight of the frame is not balanced when the detecting disc is not disposed symmetrically. It leads the frame to vibrate once the frame rotates in a high speed, which may not only cause noise but also damage the detecting disc easily. Furthermore, vibration of the frame results in misalignment between the optical pickup head and the detecting groove of the testing channel, which affects the detecting result. Therefore, there is a need to provide a solution to solve the aforementioned problems.

SUMMARY OF THE INVENTION

An objective of the present invention is to provide a rotating device for biological detection, so as to solve the aforementioned problems.

In order to achieve the aforementioned objective, a rotating device is disclosed. The rotating device is for detecting a detecting disc in biological detection. The rotating device includes a rotating shaft, a motor, a rotating disc, a left clamping disc, a right clamping disc, an upper clamping disc, and a recovering component. The motor is for rotating the rotating shaft. The rotating disc is formed in a circular shape. A center of the rotating disc is fixed on the rotating shaft. The rotating disc is rotatable along with the rotating shaft, and an engaging protrusion being disposed on a periphery of the rotating disc. The left clamping disc is located above the rotating disc and formed in a semi-circular shape. A center of a diametric side of the left clamping disc is sleeved on the rotating disc. The left clamping disc is rotatable relative to the rotating disc, and a density of the left clamping disc is half of a density of the detecting disc. The right clamping disc is located above the rotating disc and formed in a semi-circular shape. A center of a diametric side of the right clamping disc is sleeved on the rotating disc. The right clamping disc is rotatable relative to the detecting disc, and a density of the right clamping disc being half of a density of the rotating disc. The upper clamping disc is sleeved on the rotating shaft and rotatable along with the rotating disc. The upper clamping disc fixes the rotating disc, the left clamping disc, and the right clamping disc on the rotating shaft. The recovering component abuts between a side of the left clamping disc and a side of the right clamping disc for driving the other side of the left clamping disc and the other side of the right clamping disc to move toward each other. A clamping zone is formed between the other side of the left clamping disc and the other side of the right clamping disc for clamping the detecting disc, and an overlapping zone is formed between the side of the left clamping disc and the side of the right clamping disc and opposite to the clamping zone.

According to an embodiment of the present invention, the detecting disc is a circular sector corresponding to the periphery of the rotating disc, and at least one testing channel is formed on the detecting disc.

According to an embodiment of the present invention, the entire rotating disc is transparent.

According to an embodiment of the present invention, at least one part of the rotating disc corresponding to the at least one testing channel is transparent or hollow.

According to an embodiment of the present invention, the recovering component is a spring.

According to an embodiment of the present invention, the engaging protrusion is disposed on a center of an outer periphery of the clamping zone for engaging with an outer periphery of the detecting disc.

According to an embodiment of the present invention, the upper clamping disc engages with an inner periphery of the detecting disc for clamping the detecting disc in the clamping zone.

According to an embodiment of the present invention, the rotating disc supports a bottom side of the detecting disc when the detecting disc is clamped in the clamping zone.

According to an embodiment of the present invention, the other side of the left clamping disc and the other side of the right clamping disc near the clamping zone abut against two sides of the detecting disc and cooperatively clamp the detecting disc by a resilient force of the recovering component.

According to an embodiment of the present invention, a central angle of the clamping zone is equal to a central angle of the overlapping zone.

In summary, the rotating device of the present invention utilizes the left clamping disc and the right clamping disc for forming the clamping zone for clamping the detecting disc and the overlapping zone for balancing a weight of the detecting disc, which reduces vibration and enhances precision of detection. Furthermore, the central angle of the clamping zone is adjustable according to a size of the detecting disc or a number of the testing channels of the detecting disc by adjusting the left clamping disc and the right clamping disc, which increases flexibility in use.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
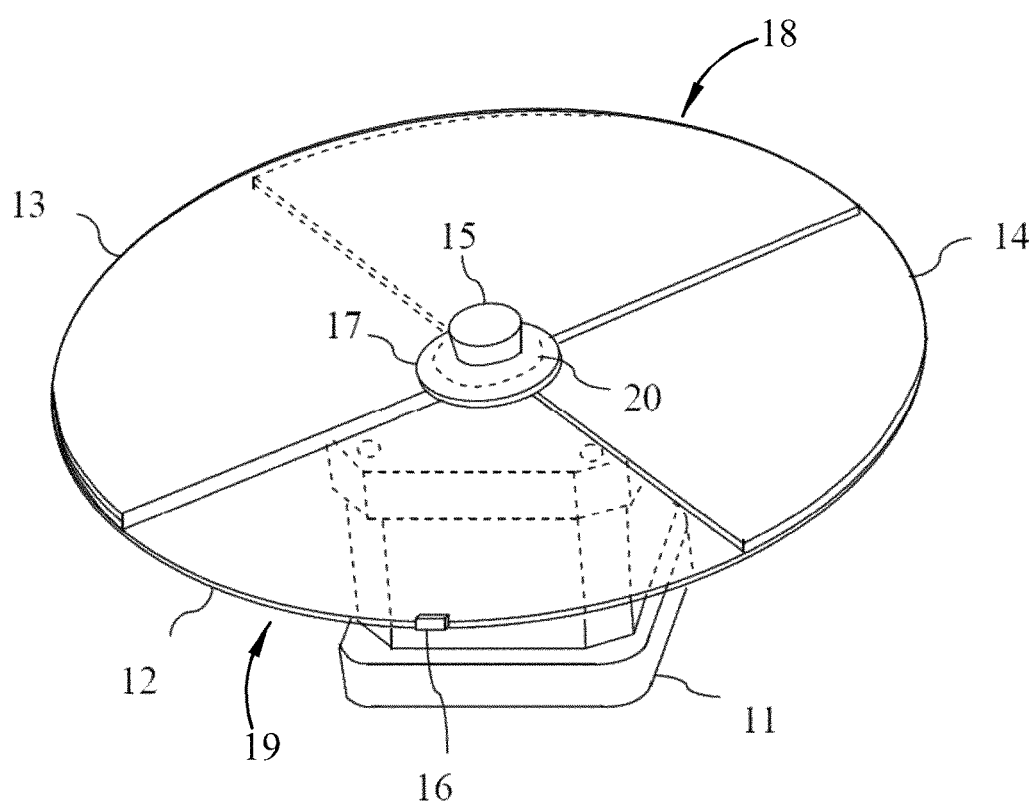
FIG. 1 is a schematic diagram of a rotating device according to an embodiment of the present invention.
Figure 2:
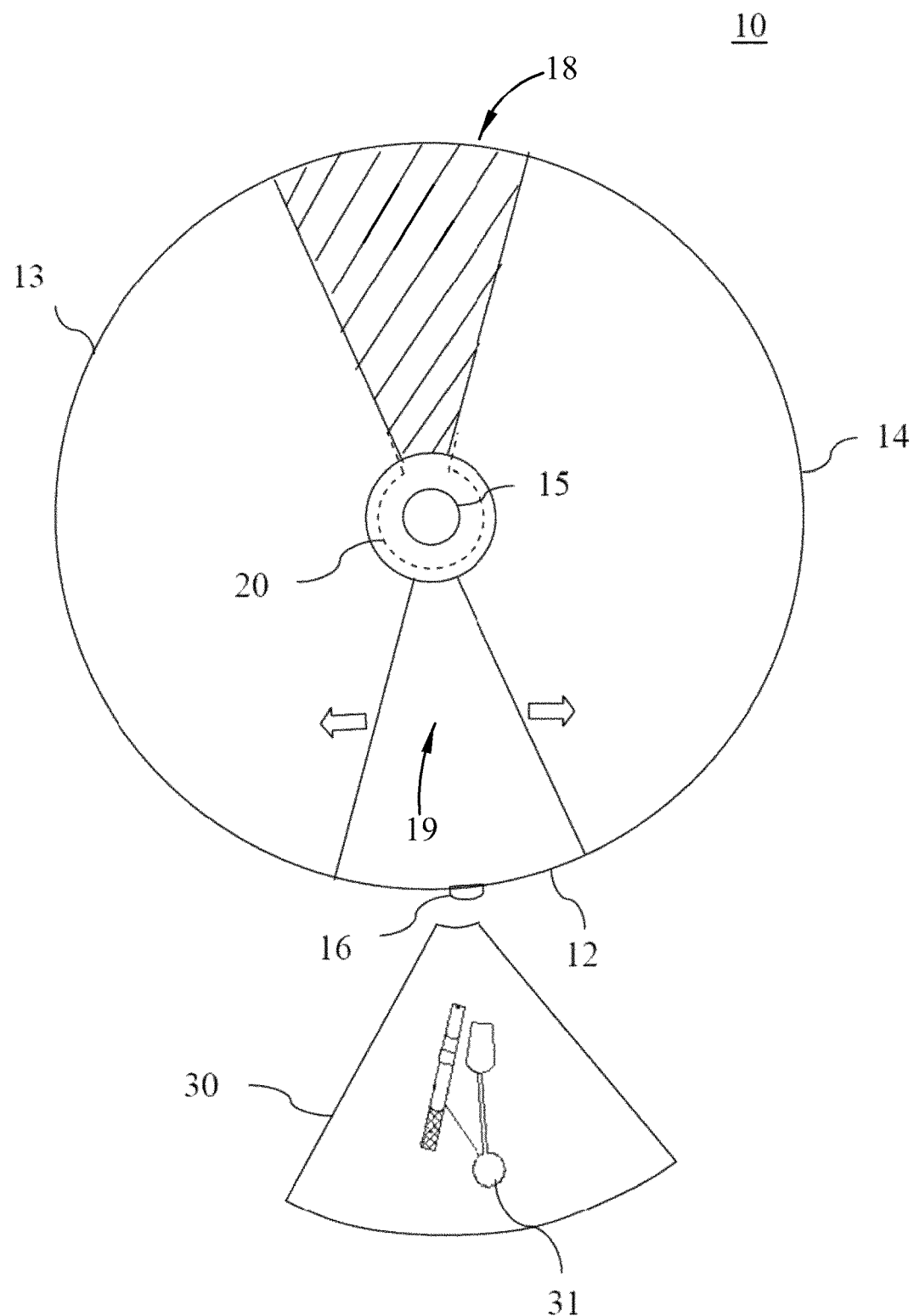
FIG. 2 is a diagram illustrating that a detecting disc has not entered a clamping zone yet according to the embodiment of the present invention.

Please refer to FIG. 1 and FIG. 2. FIG. 1 is a schematic diagram of a rotating device 10 according to an embodiment of the present invention. FIG. 2 is a diagram illustrating that a detecting disc 30 has not entered a clamping zone 19 yet according to the embodiment of the present invention. As shown in FIG. 1 and FIG. 2, the rotating device 10 is for detecting the detecting disc 30 in biological detection and includes a motor 11, a rotating disc 12, a left clamping disc 13, a right clamping disc 14, a rotating shaft 15, an engaging protrusion 16, and an upper clamping disc 17. The motor 11 drives the rotating shaft 15 to rotate. The rotating disc 12 is formed in a circular shape. The detecting disc 30 is a circular sector corresponding to a periphery of the rotating disc 12. A testing channel 31 is formed on the detecting disc 30. The entire rotating disc 12 can be transparent for optical detection. In another embodiment, at least one part of the rotating disc 12 corresponding to the testing channel 31 of the detecting disc 30 can be transparent or hollow. The engaging protrusion 16 is disposed on the periphery of the rotating disc 12. A center of the rotating disc 12 is fixed on the rotating shaft 15, so that the rotating disc 12 is rotatable along with the rotating shaft 15. Each of the left clamping disc 13 and the right clamping disc 14 can be formed in a semi-circular shape, i.e., each of the left clamping disc 13 and the right clamping disc 14 can be substantially half of the rotating disc 12. The left clamping disc 13 and the right clamping disc 14 are located above the rotating disc 12. A center of a diametric side of each of the left clamping disc 13 and the right clamping disc 14 is sleeved on the rotating shaft 15, and the left clamping disc 13 and the right clamping disc 14 are rotatable along with the rotating disc 12. The upper clamping disc 17 is sleeved on the rotating shaft 15 and located above the left clamping disc 13 and the right clamping disc 14. The upper clamping disc 17 fixes the rotating disc 12, the left clamping disc 13 and the right clamping disc 14 on the rotating shaft 15, so that the rotating disc 12, the left clamping disc 13, and the right clamping disc 14 are rotatable along with the rotating shaft 15.

It should be noticed that the left clamping disc 13 and the right clamping disc 14 are rotatable relative to the rotating disc 12. A part of the left clamping disc 13 can overlap a part of the right clamping disc 14 to form an overlapping zone 18 when the left clamping disc 13 and the right clamping disc 14 rotate relative to the rotating disc 12. That is, the overlapping zone 18 is formed between a side of the left clamping disc 13 and a side of the right clamping disc 14. On the opposite sides, the left clamping disc 13 is separated away from the right clamping disc 14, and the clamping zone 19 is formed between the other side of the left clamping disc 13 and the other side of the right clamping disc 14 for clamping the detecting disc 30. That is, the clamping zone 19 is located at a position opposite to the overlapping zone 18, such as a diagonal position. In this embodiment, the engaging protrusion 16 is preferably disposed on a center of an outer periphery of the clamping zone 19.

The rotating device 10 further includes a recovering component 20. In this embodiment, the recovering component 20 can be a spring. More specifically, the recovering component 20 abuts between the side of the left clamping disc 13 and the side of the right clamping disc 14 near the overlapping zone 18. The recovering component 20 drives the other side of the left clamping disc 13 and the other side of the right clamping disc 14 near the clamping zone 19 to move toward each other.

As shown in FIG. 2, when it is desired to detect the detecting disc 30, the left clamping disc 13 and the right clamping disc 14 are operated to overcome a resilient force of the recovering component for rotating relative to the rotating disc 12 around the rotating shaft 15, so that the clamping zone 19 is formed between the other side of the left clamping disc 13 and the other side of the right clamping disc 14 for revealing a part of the rotating disc 12. Therefore, the overlapping zone 18 is formed on a position opposite the clamping zone 19.

Figure 3:
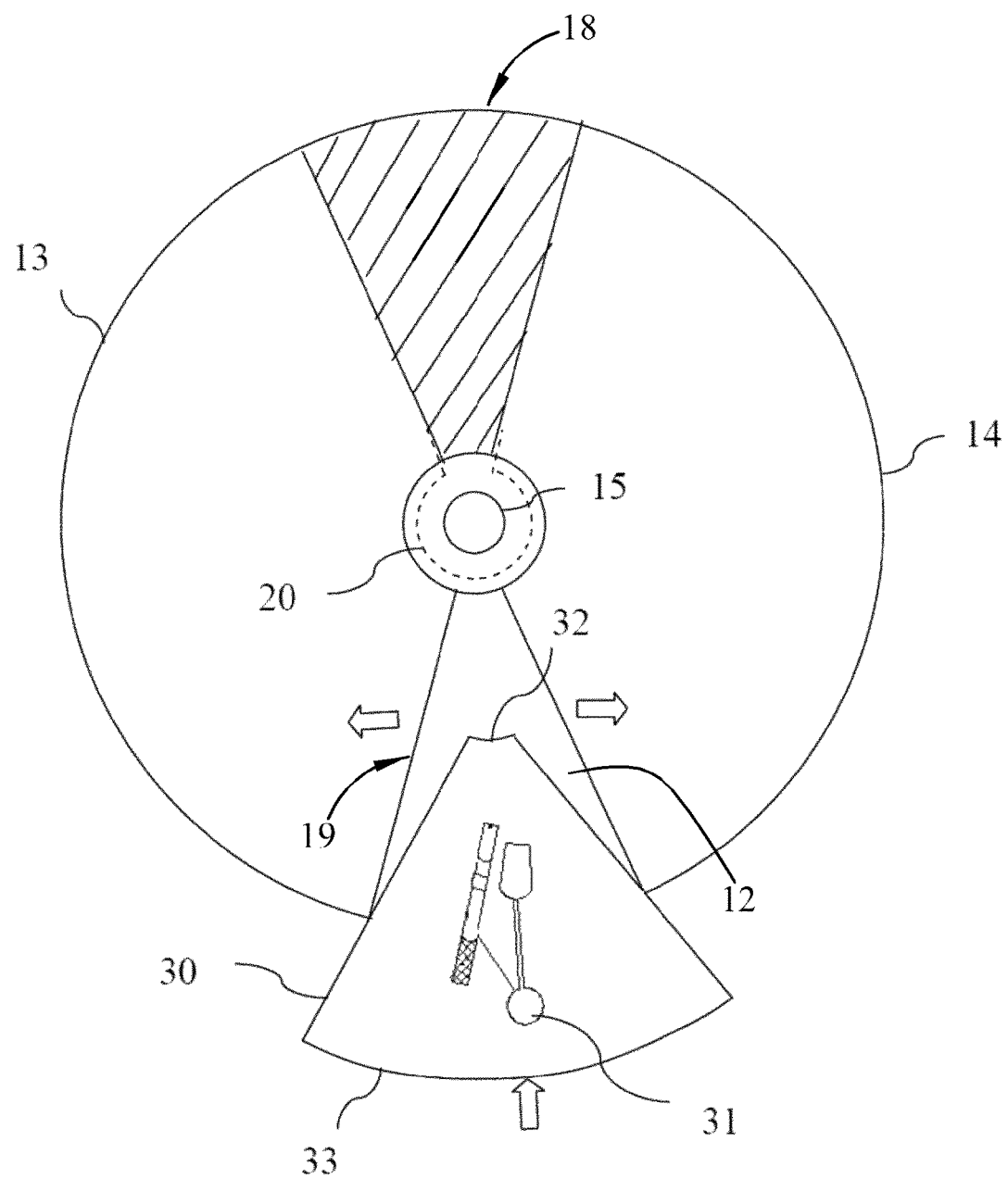
FIG. 3 is a diagram illustrating that the detecting disc is partially located within the clamping zone according to the embodiment of the present invention.

Please refer to FIG. 3. FIG. 3 is a diagram illustrating that the detecting disc 30 is partially located within the clamping zone 19 according to the embodiment of the present invention. As shown in FIG. 3, an inner periphery 32 of the detecting disc 30 is located above the exposed part of the rotating disc 12. Two sides of the detecting disc 30 abut against the other side of the left clamping disc 13 and the other side of the right clamping disc 14, respectively. When the detecting disc 30 moves inwardly by pushing an outer periphery 33 of the detecting disc 30, the two sides of the detecting disc 30 push the other side of the left clamping disc 13 and the other side of the right clamping disc 14 to move away from each other, so that the left clamping disc 13 and the right clamping disc 14 continue rotating relative to the rotating disc 12 around the rotating shaft 15 for increasing an area of the clamping zone 19 and an area of the overlapping zone 18.

Figure 4:
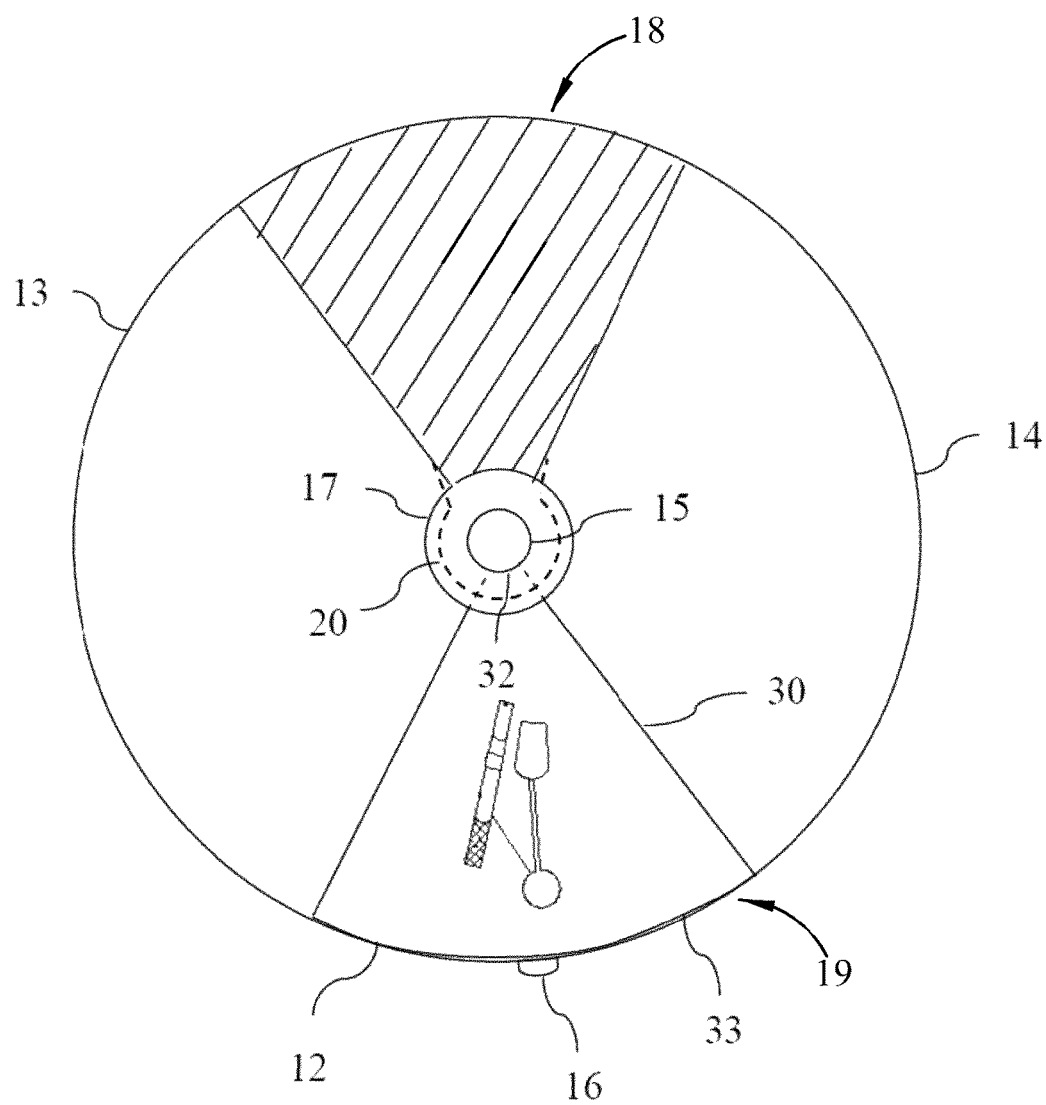
FIG. 4 is a diagram illustrating that the detecting disc is fully clamped within the clamping zone according to the embodiment of the present invention.

Please refer to FIG. 4. FIG. 4 is a diagram illustrating that the detecting disc 30 is fully clamped within the clamping zone 19 according to the embodiment of the present invention. As shown in FIG. 4, when the two sides of the detecting disc 30 push the other side of the left clamping disc 13 and the other side of the right clamping disc 14 to achieve that a central angle of the clamping zone 19 is equal to a central angle of the detecting disc 30, the detecting disc 30 is fully located within the clamping zone 19. At the same time, the area of the overlapping zone 18 is equal to an area of the detecting disc 30, too. The rotating disc 12 supports a bottom side of the detecting disc 30 when the detecting disc 30 is clamped in the clamping zone 19. The inner periphery 32 of the detecting disc 30 engages with the upper clamping disc 17. The other side of the left clamping disc 13 and the other side of the right clamping disc 14 near the clamping zone 19 abut against two sides of the detecting disc 12 and cooperatively clamp the detecting disc 30 by the resilient force of the recovering component 20. Furthermore, the outer periphery 33 of the detecting disc 30 engages with the engaging protrusion 16 disposed on the center of the outer periphery of the clamping zone 19. Therefore, the detecting disc 30 can be clamped within the clamping zone 19 firmly.

When the motor 11 drives the rotating shaft 15 to rotate the rotating disc 12, the left clamping disc 13 and the right clamping disc 14 can rotate along with the rotating disc 12. Since the detecting disc 30 is clamped within the clamping zone 19 firmly, a weight of the detecting disc 30 is preferably equal to a weight of the overlapping zone 19, so that the rotating device 10 can rotate stably. Therefore, a density of each of the left clamping disc 13 and the right clamping disc 14 is preferably half of a density of the detecting disc 30. As a result, the weight of the overlapping zone 18 formed by the part of the left clamping disc 13 and the part of the right clamping disc 14 is equal to the weight of the detecting disc 30, which allows the rotating device 10 to rotate stably and enhances precision of detection.

Figure 5:
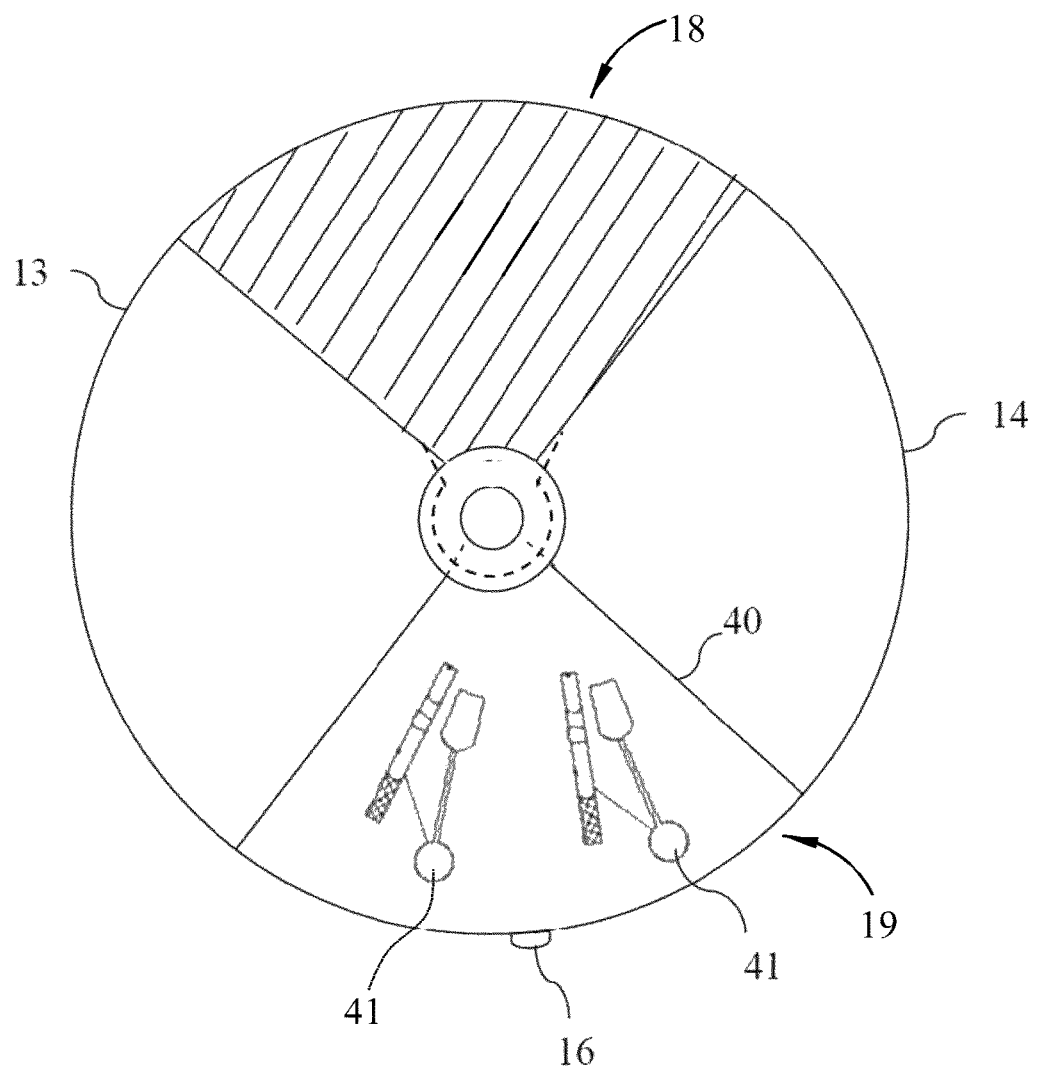
FIG. 5 is a diagram illustrating that another detecting disc is fully clamped within the clamping zone according to another embodiment of the present invention.
Figure 6:
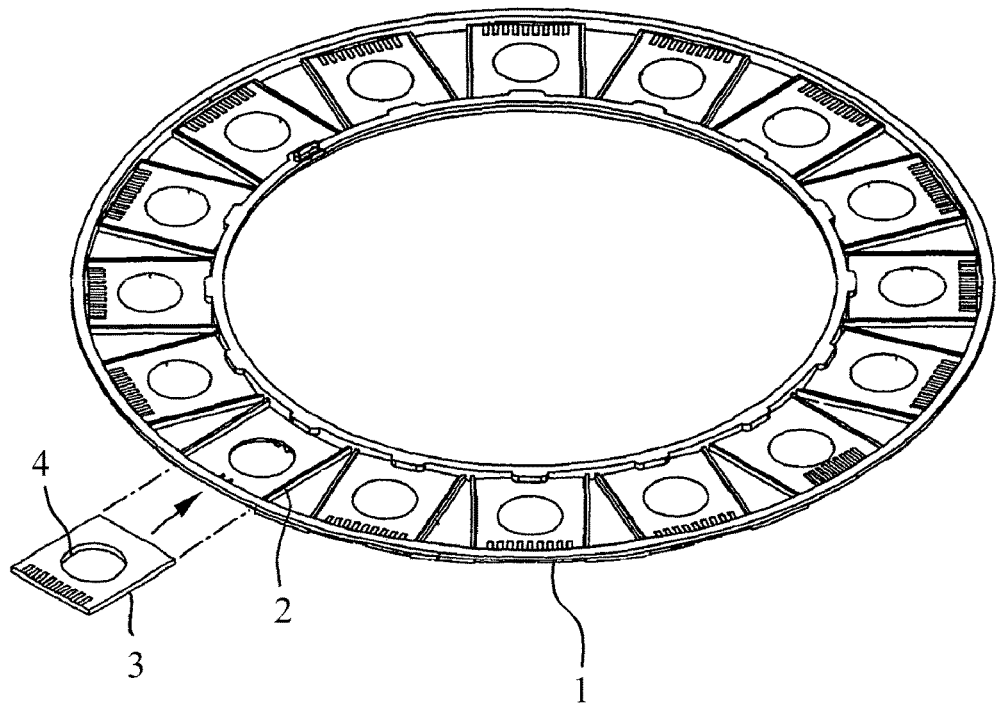
FIG. 6 is a schematic diagram of a conventional biological detection system.

Please refer to FIG. 5. FIG. 5 is a diagram illustrating another detecting disc 40 is fully clamped within the clamping zone 19 according to another embodiment of the present invention. Since the central angle of the clamping zone 19 can be adjusted by moving the left clamping disc 13 and the right clamping disc 14 for clamping the detecting disc with different central angles. Therefore, the clamping zone 19 can not only clamp the detecting disc 30 whereon only one testing channel is formed but also clamp the detecting disc 40 whereon a plurality of testing channels 41 is formed. As shown in FIG. 5, there are two testing channels 41 formed on the detecting disc 40. The central angle of the clamping zone 19 is adjustable for clamping the detecting disc 40 with a different size from a size of the detecting disc 30 by rotating the left clamping disc 13 and the right clamping disc 14 relative to the rotating disc 12. When the central angle of the clamping zone 19 is increased for receiving the detecting disc 40, the overlapping zone 18 is increased in the meantime, so that the weight of the overlapping zone 18 is equal to the weight of the detecting disc 40, which reduces vibration during rotation.

In contrast to the prior art, the rotating device of the present invention utilizes the left clamping disc and the right clamping disc for forming the clamping zone for clamping the detecting disc and the overlapping zone for balancing a weight of the detecting disc, which reduces vibration during rotation and enhances precision of detection. Furthermore, the central angle of the clamping zone is adjustable according to a size of the detecting disc or a number of the testing channels of the detecting disc by adjusting the left clamping disc and the right clamping disc, which increases flexibility in use.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A rotating device for biological detection and detecting a detecting disc, comprising:
    a rotating shaft;
    a motor for rotating the rotating shaft;
    a rotating disc formed in a circular shape, a center of the rotating disc being fixed on the rotating shaft, the rotating disc being rotatable along with the rotating shaft, and an engaging protrusion being disposed on a periphery of the rotating disc;
    a left clamping disc located above the rotating disc, the left clamping disc being formed in a semi-circular shape, a center of a diametric side of the left clamping disc being sleeved on the rotating disc, the left clamping disc being rotatable relative to the rotating disc, and a density of the left clamping disc being half of a density of the detecting disc;
    a right clamping disc located above the rotating disc, the right clamping disc being formed in a semi-circular shape, a center of a diametric side of the right clamping disc being sleeved on the rotating disc, the right clamping disc being rotatable relative to the rotating disc, and a density of the right clamping disc being half of a density of the detecting disc;
    an upper clamping disc sleeved on the rotating shaft and rotatable along with the rotating disc, the upper clamping disc fixing the rotating disc, the left clamping disc, and the right clamping disc on the rotating shaft; and
    a recovering component abutting between a side of the left clamping disc and a side of the right clamping disc for driving the other side of the left clamping disc and the other side of the right clamping disc to move toward each other;
    wherein a clamping zone is formed between the other side of the left clamping disc and the other side of the right clamping disc for clamping the detecting disc, a part of the left clamping disc overlaps a part of the right clamping disc to form an overlapping zone, and the overlapping zone is formed between the side of the left clamping disc and the side of the right clamping disc and opposite to the clamping zone.

2. The rotating device of claim 1, wherein the detecting disc is a circular sector corresponding to the periphery of the rotating disc, and at least one testing channel is formed on the detecting disc.

3. The rotating device of claim 2, wherein the entire rotating disc is transparent.

4. The rotating device of claim 2, wherein at least one part of the rotating disc corresponding to the at least one testing channel is transparent or hollow.

5. The rotating device of claim 1, wherein the recovering component is a spring.

6. The rotating device of claim 1, wherein the engaging protrusion is disposed on a center of an outer periphery of the clamping zone for engaging with an outer periphery of the detecting disc.

7. The rotating device of claim 6, wherein the upper clamping disc engages with an inner periphery of the detecting disc for clamping the detecting disc in the clamping zone.

8. The rotating device of claim 7, wherein the rotating disc supports a bottom side of the detecting disc when the detecting disc is clamped in the clamping zone.

9. The rotating device of claim 8, wherein the other side of the left clamping disc and the other side of the right clamping disc near the clamping zone abut against two sides of the detecting disc and cooperatively clamp the detecting disc by a resilient force of the recovering component.

10. The rotating device of claim 1, wherein a central angle of the clamping zone is equal to a central angle of the overlapping zone.

* * * * *